United States Patent [19]

DePriest

[11] Patent Number: 4,940,807

[45] Date of Patent: Jul. 10, 1990

[54] SELECTIVE BROMINATION OF AROMATIC COMPOUNDS USING POTASSIUM TRIBROMIDE

[75] Inventor: Robert N. DePriest, Columbia, S.C.

[73] Assignee: Ethyl Corporation, Richmond, Va.

[21] Appl. No.: 365,209

[22] Filed: Jun. 12, 1989

[51] Int. Cl.$^5$ .................. C07D 317/62; C07C 43/225
[52] U.S. Cl. ..................... 549/434; 568/649; 568/663; 568/656; 568/779; 568/765
[58] Field of Search ............... 549/434; 568/663, 649, 568/779, 765, 656; 570/206; 564/442

[56] References Cited

U.S. PATENT DOCUMENTS 3,689,559  9/1972  Taylor et al. ................ 568/649
4,822,930  4/1989  Liu ............................ 570/206

*Primary Examiner*—Nicky Chan
*Attorney, Agent, or Firm*—John F. Sieberth

[57] ABSTRACT

Electron-rich aromatic compounds are selectively brominated in good yield in the presence of water using potassium tribromide as the brominating agent. In this way monobromination is favored and dibromination is suppressed as compared to the use of elemental bromine as the brominating agent.

12 Claims, No Drawings

SELECTIVE BROMINATION OF AROMATIC COMPOUNDS USING POTASSIUM TRIBROMIDE

TECHNICAL FIELD

This invention relates to the selective monobromination of electron-rich aromatic compounds, that is, compounds in which the benzene nucleus is substituted by one or two activating groups of high polarity, such as hydroxy, alkoxy, amino, alkylamino, dialkylamino, and the like.

BACKGROUND

Electron-rich aromatic compounds such as phenols, aromatic amines, alkyl aryl ethers, etc. tend to undergo multiple bromination when treated with elemental bromine under the usual bromination conditions. In many instances, however, it is desired to introduce but one bromine atom into the aromatic nucleus of such compounds. This invention is deemed to provide a highly efficacious method for achieving such monobromination in high yield and selectivity while minimizing the extent to which polybromination of the ring occurs.

THE INVENTION

In accordance with this invention ring-brominatable electron-rich aromatic compounds are reacted with potassium tribromide in the presence of water such that a product enriched in monobromo ring substitution is formed. The extent to which multiple ring bromination occurs in the process is effectively suppressed.

The process is advantageous in a number of other respects. In the first place, potassium tribromide is readily formed by combining equimolar or substantially equimolar proportions of elemental bromine and potassium bromide in an aqueous medium. Moreover in most cases the reaction is slightly exothermic, and thus the process can be conducted at ambient temperatures—application of heat is ordinarily unnecessary. Further, potassium bromide is readily regenerated by the addition of potassium hydroxide to the by-product hydrogen bromide solution.

If desired, the bromination reaction medium may include organic solvents or diluents, such as methylene dibromide, 1,2-dibromoethane, chlorobenzene, methylene dichloride, carbon tetrachloride, 1,2-chloroethane, hexane, heptane, octane, decane, cyclohexane, toluene, xylene, or the like.

The process may be applied to any of a wide variety of electron-rich aromatic compounds so long as the activated benzene ring system has at least two positions in which bromination can occur. A few illustrative compounds of this type include phenol, cresol, the xylenols, resorcinol, hydroquinone, the trihydroxybenzenes, aniline, N-methylaniline, N,N-dimethylaniline, p-phenylenediamine, diphenylamine, anisole, hydroxyanisole, ethoxybenzene, aminophenol, and the like.

As noted above, the reaction is preferably conducted at ambient temperatures but where deemed necessary or desirable the reaction system may be heated or cooled so that the reaction takes place under optimal reaction conditions. Ordinarily reaction temperatures will fall within the range of about 0 to about 35° C., it being understood however that departures from this range are permissible whenever such departures are deemed necessary or appropriate.

Monobrominated aromatic compounds are of considerable utility in the chemical and allied arts. For example, they serve as excellent intermediates for a variety of well-known reactions such as Wurtz-type condensation reactions, hydrolysis reactions, formation of Grignard reagents, and many other useful syntheses. The process of this invention thus makes possible the selective formation of compounds useful in the synthesis of pharmaceuticals, dyestuffs, fragrance materials, pesticides, polymers, and many other useful products.

The practice and advantages of this invention are illustrated by the following examples.

EXAMPLE 1

Pursuant to this invention 2-bromo-1,4-dimethoxybenzene, a useful intermediate for the synthesis of the pharmaceutical intermediate 2,5-dimethoxybenzaldehyde, was produced in the following manner: Into a 500 mL round bottom flask were charged 100 grams of 1,4-dimethoxybenzene and 100 grams of methylene dibromide. An endotherm to 12° C. occurred when creating this solution. Separately prepared was a solution of 90 grams of KBr in 265 grams of water to which was added 35.5 mL of bromine, and the resulting mixture was stirred to form an aqueous solution of $KBr_3$. A portion of this solution (250 mL) was added slowly to the 1,4-dimethoxybenzene solution. After a slight exotherm from 13° to 22° C. occurred (in 20 minutes) a cooling water bath was applied externally to the flask to keep the temperature at 22°–25° C. The total feed time was 70 minutes. The bromine color disappeared within 10 minutes after the addition had been completed. To dissolve some salts that appeared in the reaction mixture, 60 mL of water was added thereto. The phases were separated in a separatory funnel and the aqueous layer was discarded. The organic phase was washed with 30 grams of 10% sodium carbonate solution (pH 7–10) and the phases separated readily. The product solution was stripped at reduced pressure to 65° C. at 0.5 mm Hg pressure, distilled and subjected to analysis.

EXAMPLE 2

The same general procedure as in Example 1 was again used to produce 2-bromo-1,4-dimethoxybenzene using $KBr_3$ as the brominating agent.

COMPARATIVE EXAMPLE A

The general procedure of Example 1 was repeated except that besides the 1,4-dimethoxybenzene and methylene dibromide 125 grams of water was included in the initial charge to the flask, 104 grams of elemental bromine was slowly fed to the stirred reaction mixture, and the temperature was controlled to 0°–10° C. by means of an external ice bath. The product was subjected to a similar work-up procedure, and analyzed by gas chromatography.

COMPARATIVE EXAMPLE B

Comparative Example A was repeated in essentially the same manner except that the reaction was conducted at half the scale previously used.

The analyses of the product solutions formed in Examples 1 and 2, and in Comparative Examples A and B, are summarized in the following table wherein the following acronyms are used: DMB=1,4-dimethoxybenzene, BDMB=2-bromo-1,4-dimethoxybenzene, DBDMB=ar-dibromo-1,4-dimethoxybenzene.

| Bromine | Results | | | |
|---|---|---|---|---|
| Reagent | DMB | BDMB | DBDMB | BDMB/DBDMB Ratio |
| KBr$_3$ | 10.4% | 79.8% | 8.3% | 9.6 |
| KBr$_3$ | 14.8% | 76.0% | 9.1% | 8.4 |
| Br$_2$ | 30.0% | 48.0% | 22.0% | 2.2 |
| Br$_2$ | 29.9% | 41.3% | 28.7% | 1.4 |

EXAMPLE 3

Into a 500mL three-necked flask equipped with a dropping funnel, condenser, thermometer and mechanical stirrer were charged 50 grams of methylene-1,2-dioxybenzene (MDOB), 50 grams of methylene dibromide (Me$_2$Br$_2$) and 20 grams of 34% aqueous potassium bromide. With stirring, an aqueous potassium tribromide solution—formed from 165 grams of 34% aqueous KBr and 65 grams of elemental bromine—was added slowly over a two-hour period during which time the mildly exothermic reaction kept the reaction mixture at or slightly below 30° C. Samples were taken when 25%, 50%, 75% and 100% of the aqueous KBr$_3$ solution had been added in order to determine the extent to which monobromination to methylene-1,2-dioxy-4-bromobenzene (BrMDOB) and dibromination to Br$_2$MDOB had occurred. Another sample was taken after stirring the final reaction mixture for 30 minutes. Gas chromatographic analysis of these samples gave the following results (expressed in terms of percentages of the designated materials present):

| | 25% | 50% | 75% | 100% | After 30 min. |
|---|---|---|---|---|---|
| Me$_2$Br$_2$ | 32.6 | 30.6 | 28.64 | 26.7 | 27.7 |
| MDOB | 48.93 | 29.5 | 15.3 | 7.8 | 8.54 |
| BrMDOB | 17.88 | 39.2 | 55.1 | 63.8 | 61.6 |
| Br$_2$MDOB | 0.36 | 0.49 | 0.7 | 1.4 | 1.53 |

The final product mixture was quenched with 25 grams of water, and the aqueous and organic phases were separated from each other. The organic phase was treated with 20 grams of 15% aqueous bisulfite solution and the pH was adjusted by addition of 10% aqueous NaOH solution. A clean phase separation was effected and the isolated product of the organic phase contained 12.5% MDOB, 84.9% BrMDOB and 2.5% Br$_2$MDOB.

It is of interest to note that BrMDOB is a useful intermediate in the synthesis of heliotropin, a fragrance material. The synthesis involves reacting the Grignard reagent formed from BrMDOB with N,N-dimethylformamide.

EXAMPLE 4

The general procedure of Example 3 was repeated except that the organic co-solvent (methylene dibromide) was not used, and a sample was not taken for analysis at the 50% addition point. The initial charge to the flask was the same as in Example 2 (absent the Me$_2$Br$_2$) and the aqueous KBr$_3$ feed to the flask in this case was formed from 173 grams of the 34% aqueous KBr solution and 68 grams of elemental bromine. The work up procedure after the 30 minute ride period involved a 50 gram water quench, phase separation, a wash of the separated organic phase with approximately 20 mL of 15% sodium bisulfite, then a wash of the organic phase with 10% sodium carbonate solution (approximately 20 mL) to a pH of 8-9. A total of 70.1 grams of crude product was isolated. The gas chromatographic analyses were as follows:

| | 25% | 75% | 100% | 30 min. | Isolated Product |
|---|---|---|---|---|---|
| MDOB | 69.9 | 28.8 | 6.8 | 6.9 | 6.8 |
| BrMDOB | 28.9 | 69.5 | 88.3 | 88.2 | 87.9 |
| Br$_2$MDOB | 0.85 | 1.2 | 4.4 | 4.4 | 5.0 |

EXAMPLE

Elemental bromine (3.5 mL) was added to 25 grams of a 34% aqueous KBr solution to form a solution of KBr$_3$. This solution was added to 8.5 grams of MDOB in 10 grams of Me$_2$Br$_2$ at room temperature over a 10-minute period. Five minutes later the reaction mixture was quenched with aqueous sodium bisulfite solution. Gas chromatographic analysis of the reaction product mixture showed 14.0% MDOB, 81.8% BrMDOB and 4.3% Br$_2$MDOB.

The following Comparative Examples C, D, E and F, wherein all parts are by weight, illustrate the extent to which Br$_2$MDOB is produced when using elemental bromine in lieu of KBr$_3$ as the brominating agent.

COMPARATIVE EXAMPLE C

Methylene dibromide (108 parts) and MDOB (108 parts) were placed in a reactor and agitated with external cooling. Bromine (138 parts) was metered into the reactor over a 220 minute period, while keeping the mixture in the range of 23-36° C. After an additional hour, sodium bisulfite (30 parts of 15% aqueous solution) was added, the phases were separated, and the product solution was adjusted to pH 7-8 with sodium carbonate (30 parts of 15% aqueous solution). The crude product (257 parts), which analysed 37% Me$_2$Br$_2$, 7.4% MDOB, 45.6% BrMDOB and 10.0% Br$_2$MDOB prior to distillation, thus contained BrMDOB and Br$_2$MDOB in a weight ratio of 82% BrMDOB and 18% Br$_2$MDOB.

COMPARATIVE EXAMPLE D

To a reactor equipped with a water scrubber for HBr by-product were charged 100 grams of methylene dichloride and 100 grams of MBOB. While continuously stirring the reaction mixture, 131 grams of elemental bromine was added portionwise over a period of 106 minutes during which time the temperature of the reaction mixture was between 23 and 30° C. After an additional 10 minute period, the product mixture was quenched by addition of 25 mL of 20% sodium bisulfite solution, the phases were separated, and the product solution was washed with 25 mL of 20% sodium carbonate solution. Again the phases were separated and the product solution was stripped at reduced pressure (to 70 mm Hg at 170° C.). Analysis of the residual solution showed it to contain 5.05% MDOB, 83.1% BrMDOB and 11.8% Br$_2$MDOB.

COMPARATIVE EXAMPLE E

The procedure of Comparative Example D was repeated using a mixture of 100 grams of chlorobenzene and 33 grams of water as the solvent system instead of methylene dibromide. The bromine addition occurred over a period of 90 minutes and was followed by an additional 30 minute ride period. During the bromine addition the temperature remained between 25° and 27°

C. The product distribution after work-up was found to be essentially the same as in Comparative Example C.

COMPARATIVE EXAMPLE F

In another run similar to those of Comparative Examples D and E, 25.0 grams of MDOB in 25.0 grams of methylene dibromide was treated with 10 mL of bromine over a 25-minute period. An exotherm from 22° to 36° C. occurred. After a 30 minute digestion period the product mixture was quenched by addition to aqueous sodium bisulfite solution. Gas chromatographic analysis showed the product mixture contained 10.8% MDOB, 75.3% BrMDOB and 13.9% $Br_2$MDOB.

While it is preferred to feed the $KBr_3$ aqueous solution to the aromatic compound undergoing bromination, and to conduct such feed on a continuous or interrupted portionwise basis, it is possible to conduct the process in other ways such as by cofeeding the reactants into the reaction zone. These and other variants will be apparent to those skilled in the art, from a reading of the present description. Usually the molar ratio of $KBr_3$:aromatic compound will fall in the range of about 0.5:1 to about 1:1, but deviations from this range may be found suitable.

This invention is susceptible to considerable variation in its practice within the spirit and scope of the ensuing claims, and it is not intended that this invention be limited by the illustrative exemplifications presented hereinabove.

What is claimed is:

1. A process which comprises reacting a ring-brominatable electron-rich aromatic compound with potassium tribromide in the presence of water such that a product enriched in monobromo ring substitution is formed.

2. A process of claim 1 wherein the reaction mixture also includes an ancillary organic solvent or diluent.

3. A process of claim 1 wherein the reaction is performed predominantly at a temperature within the range of about 0 and about 35° C.

4. A process of claim 1 wherein the potassium tribromide is fed portionwise as an aqueous solution to the reaction mixture while agitating the reaction mixture, the feed being terminated when the molar ratio of potassium tribromide to the aromatic compound undergoing bromination falls within the range of about 0.5:1 and about 1:1.

5. A process of claim 1 wherein the aromatic compound undergoing bromination is an alkoxyaromatic compound.

6. A process of claim 1 wherein the aromatic compound undergoing bromination is an alkylene-1,2-dioxyaromatic compound.

7. A process which comprises reacting 1,4-dimethoxybenzene with potassium tribromide in the presence of water such that a product enriched in 2-bromo-1,4-dimethoxybenzene is formed and the formation of dibromo-1,4-dimethoxybenzene is suppressed.

8. A process of claim 7 wherein the reaction mixture also includes an ancillary organic solvent or diluent.

9. A process of claim 7 wherein the reaction is performed predominantly at a temperature within the range of about 0 and about 35° C.

10. A process which comprises reacting methylene-1,2-dioxybenzene with potassium tribromide in the presence of water such that a product enriched in methylene-1,2-dioxy-monobromobenzene is formed and the formation of methylene-1,2-dioxydibromobenzene is suppressed.

11. A process of claim 10 wherein the reaction mixture also includes an ancillary organic solvent or diluent.

12. A process of claim 10 wherein the reaction is performed predominantly at a temperature within the range of about 0 and about 35° C.

* * * * *